US00PP19950P3

(12) United States Plant Patent

Werner et al.

(10) Patent No.: US PP19,950 P3

(45) Date of Patent: Apr. 21, 2009

(54) *BUDDLEJA* PLANT NAMED 'MISS RUBY'

(50) Latin Name: *Buddleja*
Varietal Denomination: Miss Ruby

(75) Inventors: Dennis James Werner, Raleigh, NC (US); Layne Karlton Snelling, Cary, NC (US)

(73) Assignee: North Carolina State University, Raleigh, NC (US)

( * ) Notice: Subject to any disclaimer, the term of this patent is extended or adjusted under 35 U.S.C. 154(b) by 69 days.

(21) Appl. No.: 11/894,866

(22) Filed: Aug. 23, 2007

(65) Prior Publication Data

US 2009/0055980 P1 Feb. 26, 2009

(51) Int. Cl.
*A01H 5/00* (2006.01)

(52) U.S. Cl. ..... Plt./242

(58) Field of Classification Search ..... Plt./242
See application file for complete search history.

(56) References Cited

PUBLICATIONS

UPOV ROM GTITM Computer Database, GTI Jouve Retrieval Software 2008/01 Citation for 'Miss Ruby'.*

* cited by examiner

*Primary Examiner*—Wendy C. Haas

(57) ABSTRACT

*Buddleja* 'Miss Ruby' is a new and distinct variety of butterfly bush that has the following unique combination of desirable features that are outstanding in a new variety.

1. Moderate vigor resulting in compact growth habit.
2. Ease of asexual propagation using softwood or semi-hardwood cuttings.
3. Upright growth habit with flowers borne stiffly on upright shoots.
4. Low female fertility and reduced seed set, resulting in less opportunity for seedlings to originate in the landscape setting.
5. Bright pink flower color, unknown in any other butterfly bush variety known to the inventor.

3 Drawing Sheets

Latin name of the genus and species: Genus: *Buddleja.* Species: complex hybrid including *davidii, globosa,* and *fallowiana.*

Variety denomination:

The inventive cultivar of *Buddleja* disclosed herein has been given the variety denomination 'Miss Ruby'.

BACKGROUND OF THE INVENTION

The present invention relates to a new and distinct variety of *Buddleja* (butterfly bush) grown as an ornamental shrub for home and commercial landscapes. Butterfly bush is typically grown for its attractive, fragrant flowers that are borne throughout the growing season.

The new and distinct variety of butterfly bush resulted from a formal breeding program established by the inventors in Raleigh, N.C., United States. One of the objectives of the breeding program was to develop a compact *Buddleja* with bright pink flower color. 'Miss Ruby' originated as a first generation descendant from a hand pollinated cross of *Buddleja* 'White Ball' butterfly bush (non-patented)× *Buddleja* 'Attraction' butterfly bush (non-patented) made in 2002 'White Ball' was released and named as a butterfly bush cultivar by in Booskoop, The Netherlands, in 1974, and is available in commerce. The 'Attraction' parent used in this hybridization was released in 2001. Both 'Attraction' and 'White Ball' are complex hybrids comprised of multiple species of *Buddleja,* and hence assigning a species designation to either cultivar is inappropriate.

The seeds resulting from the 2002 controlled hybridization process were harvested in fall of 2002 and germinated in a greenhouse in Raleigh, N.C. in the winter of 2003. The resulting seedlings were planted in field trials in spring of 2003. These plants flowered in summer 2003, and one seedling, designated NC2003-22, was selected for its compact growth habit, attractive gray-green leaf color, and attractive bright pink flower color. This original plant demonstrated characteristics identical to those subsequently expressed on other plants when propagated from stem cuttings. This single plant is the subject of the present invention 'Miss Ruby'.

The distinguishing traits of 'Miss Ruby' are compact growth habit, gray-green leaf color, and flowers that are bright pink in color. The cultural requirements for 'Miss Ruby' are well-drained soil, full sun, and moderate moisture. 'Miss Ruby' exhibits no serious pest or disease problems known to the inventors, except for occasional spider mite infestation during periods of hot, dry weather.

The closest comparison known to the inventors are the parents 'White Ball' and 'Attraction'. Plants and flowers of this new variety differ from its parents. 'Miss Ruby' produces a plant that is similar to the 'White Ball' parent in size and stature, but possesses bright pink rather than the white flowers of 'White Ball'. 'Miss Ruby' is different than the 'Attraction' parent in being more compact in growth, and having bright pink flower color, as compared to the red-purple of 'Attraction'.

The first asexual propagation of 'Miss Ruby' was conducted by the inventors in fall 2003 in Raleigh, N.C., and 'Miss Ruby' has subsequently been propagated in the same location in years 2004 and 2006. In all cases, the original plant selection was propagated asexually by softwood to semi-hardwood stem cuttings. Such cuttings root readily under mist in about 14 to 21 days, and resume normal growth. Four plants derived from stem cuttings of the variety were established in 2005, and ten additional plants derived from stem cuttings of the variety were established in 2007. During all asexual propagation, the characteristics of the original plant have been maintained. Plants derived from stem cuttings exhibit characteristics identical to those of the original plant, and no aberrant phenotypes have appeared.

Test plantings and performance evaluation over three years demonstrate this variety to be relatively consistent in its characteristics even under the different growing conditions associated with yearly climatic variation.

Plants of the new variety are only moderately vigorous after establishment in the field, being less vigorous and more compact than most cultivars of butterfly bush. Young plants have averaged about 0.5 meters of growth per year. Plants are semi-upright in growth habit. Flowering occurs in the first year of growth on newly formed wood. The inflorescence is a simple panicle, and shows a unique bright pink flower color. Flowering usually begins in late May to early June in Jackson Springs, N.C., and continues throughout the growing season until the first freeze event in October or November. An individual inflorescence flowers for about 7–10 days, depending on temperature, but new flowers are made during the entire growing season. Fertility of flowers is low, and the new cultivar sets very few seed, an asset in landscape settings.

'Miss Ruby' is distinguished from other related known cultivars based on the unique combination of traits including compact growth habit, gray-green leaf color, and bright pink flower color.

The new variety has been named the MISS RUBY cultivar. No public sale of 'Miss Ruby' has yet taken place at the time of application.

SUMMARY OF THE INVENTION

'Miss Ruby' is a new and distinct variety of butterfly bush that has the following unique combination of desirable features outstanding in a new variety. In combination these traits set 'Miss Ruby' apart from all other existing varieties of butterfly bush known to the inventors.

1. 'MISS RUBY' has moderate vigor resulting in compact growth habit.
2. 'MISS RUBY' is asexually propagated using softwood or semi-hardwood cuttings.
3. 'MISS RUBY' demonstrates upright growth habit with flowers borne stiffly on upright shoots.
4. 'MISS RUBY' exhibits low female fertility and reduced seed set, resulting in less opportunity for seedlings to originate in the landscape setting.
5. 'MISS RUBY' has bright pink flower color, unknown in any other butterfly bush variety.

BRIEF DESCRIPTION OF THE DRAWINGS

The photographs in the drawings were made using digital photography techniques, and show the colors as true as reasonably possible by digital photography. Colors in the photographs may differ slightly from the color values cited in the detailed botanical description, which accurately describe the colors of the new *Buddleja* variety 'MISS RUBY'. All photographs were taken from two-year-old plants growing Jackson Springs, N.C.

The first drawing shows a typical plant of 'MISS RUBY', showing the compact growth, upright habit, and unique bright pink flowers.

The second drawing shows a close-up view of the inflorescence of 'MISS RUBY', showing the unique bright pink color of the individual flowers in the inflorescence.

The third drawing shows the typical coloration and form of leaves of 'MISS RUBY'. This figure shows the lower and upper leaf surface.

DETAILED BOTANICAL DESCRIPTION OF THE VARIETY

The following is a detailed description of the botanical and ornamental characteristics of the subject butterfly bush 'MISS RUBY'. Color data are based on *The Royal Horticultural Society Colour Chart,* The Royal Horticultural Society, London, 2001 edition. Where dimensions, sizes, colors and other characteristics are given, it is to be understood that such characteristics are approximations of averages set forth as accurately as practicable.

The descriptions reported herein are from two-year-old specimens grown out-of-doors in Raleigh, N.C.

Genus: *Buddleja.*
Species: complex hybrid comprised of *Buddleja davidii, Buddleja globosa,* and *Buddleja fallowiana.*
Denomination: 'MISS RUBY'.
Commercial Classification: Shrub, deciduous.
Common name: Butterfly bush.
Type: Ornamental.
Uses: Patio container plant, herbaceous perennial border, or shrub border for residential and commercial landscapes.
Cultural requirements: Full sun exposure, well-drained soil, and moderate moisture.
Parentage: 'MISS RUBY' is a hybrid that resulted from the cross pollination of the following *Buddleja* parents: Seed parent='White Ball'. Pollen parent='Attraction'.
Plant description:

*Blooming period.*—Spring, summer, and early fall until frost.
*Blooming habit.*—Upright with narrow flowers.
*Vigor.*—Low vigor.
*Plant habit.*—Compact, spreading habit.
*Height and spread.*—0.83 meters (height) and 1.4 meters (width).
*Hardiness.*—To date, hardy to minus 8 degrees Centigrade. Not tested below this temperature. Anticipated adapted from USDA hardiness zones 5–9.
*Propagation.*—Softwood to semi-hardwood cuttings under intermittent mist. Roots typically form in 2–3 weeks.
*Root system.*—Fibrous.
*Seasonal interest.*—Bright pink flowers in spring, summer, and fall on a compact shrub.
*Disease and pest susceptibility and resistance.*—No particular susceptibility or resistance, except occasionally susceptible to spider mites under very hot and dry conditions.
*Special growing requirements.*—Severe yearly pruning in late winter or early spring prior to bud break is recommended to encourage more profuse flowering.

Stems:

*Shape.*—Stem cross section is quadrangular.
*Length.*—Average 53 cm.

*Color.*—Yellow-green (RHS 144C) on recently formed shoots.
*Diameter.*—3 mm. near terminal portion of stem, and 20 mm. near base of stem.
*Stem surface.*—Glaucous.
*Pubescence.*—Absent.
*Internode length.*—4.0 cm. between nodes Foliage:
*Type.*—Deciduous.
*Leaf arrangement.*—Opposite, decussate.
*Leaf division.*—Simple.
*Leaf shape.*—Elliptic.
*Leaf base.*—Attenuate.
*Leaf apex.*—Acuminate.
*Leaf venation.*—Pinnate.
*Leaf surface* (*abaxial*).—Glaucous.
*Leaf margin.*—Serrulate.
*Leaf attachment.*—Petiolate.
*Petiole dimensions.*—3.4 mm length. 1.2 mm. width.
*Petiole shape.*—Sulcate.
*Petiole color.*—Grayed-green (RHS 194C).
*Leaf color.*—Adaxial side=green (RHS 137A). Abaxial side=grayed-green (RHS 194B).
*Leaf length.*—Average length (10 leaves)=6.7 cm.
*Leaf width.*—Average width (10 leaves) 1.8 cm.
*Foliar fragrance.*—None detectable.

Flowers:
*Inflorescence.*—Terminal panicle.
*Petals.*—4 in number.
*Fused or unfused.*—Fused at base.
*Petal margin.*—Entire.
*Petal apex.*—Rounded lobes, serrulate.
*Petal base.*—Truncate.
*Petal surfaces.*—Glaucous.
*Petal shape.*—Rotund.
*Petal dimensions.*—8 mm. length. 1.2 mm. width.
*Petal color.*—Adaxial and abaxial surface=red-purple (RHS 71B to 71C).
*Flower shape.*—Salverform.
*Corolla tube color.*—Inside surface=orange (RHS 25A).
*Corolla tube surfaces* (*inner and outer surfaces*).—Pubescent.
*Corolla tube shape.*—Tubular.
*Color of peduncle.*—Grayed-green (RHS 191B).
*Peduncle surface.*—Glaucous.
*Peduncle length.*—1.4 cm.
*Peduncle shape.*—Flattened oval in cross section.
*Pedicel dimensions.*—1.0 mm. in length and less than 1 mm. in diameter.
*Pedicel color.*—Grayed-green (RHS 191B).
*Pedicel shape.*—Flattened oval in cross section.
*Pedicel surface.*—Glaucous.
*Flowers persistent or self-cleaning.*—Flowers are persistent.
*Lastingness of the overall inflorescence.*—3 –4 weeks.
*Lastingness of an individual flower.*—3–5 days.
*Dimensions of inflorescence.*—10.6 cm. in length. 3.0 cm. in diameter.
*Dimensions of entire individual flower.*—12 mm. length. Diameter 12 mm. at apex tapering to 1 mm. at base.
*Quantity of flowers.*—140 to 160 flowers per individual inflorescence.
*Bud color.*—Red-purple (RHS 71A).
*Bud apex.*—Rounded.
*Bud surface.*—Glabrous.
*Bud shape.*—Elongated, linear balloon.
*Calyx shape.*—Tubular.
*Calyx dimensions.*—1.0 mm. in width and 3.0 mm. in length.
*Sepal.*—Four in number.
*Sepal shape.*—Lanceolate.
*Sepal apex.*—Acute.
*Sepal margin.*—Entire.
*Sepal surface.*—Glabrous.
*Sepal color.*—Grayed-green (RHS 191B).
*Flower fragrance.*—Distinct sweet fragrance.

Reproductive organs:
*Stamens.*—Four, fused to inside of petals.
*Anther shape.*—Oblong.
*Anther dimensions.*—1 mm. in length and 0.2 mm. wide.
*Filament size.*—5 mm. in length and less than 0.5 mm. in width.
*Filament color.*—Red-purple (RHS 69D).
*Pollen amount.*—Low. Some flowers produce none.
*Pollen color.*—Yellow-white (RHS 158D).
*Pistil.*—One in number.
*Pistil dimensions.*—4 mm. in length, and less than 1 mm. in diameter.
*Stigma color.*—Yellow-green (RHS 144A).
*Ovary.*—Present.
*Ovary position.*—Superior.
*Ovary shape.*—Oval.
*Fertility.*—Self-unfruitful. Requires cross pollination. Low female fertility.

Fruit:
*Type.*—Swelled capsule.
*Dimensions.*—7.5 mm. in length (variable) and 1.9 mm. in diameter (variable).
*Color.*—Yellow-green (RHS 144C) when immature.

That which is claimed is:

1. A new and distinct variety of butterfly bush (*Buddleja*) substantially as illustrated and described, characterized by its compact growth habit, grayed-green leaf color, and bright pink flower color.

* * * * *

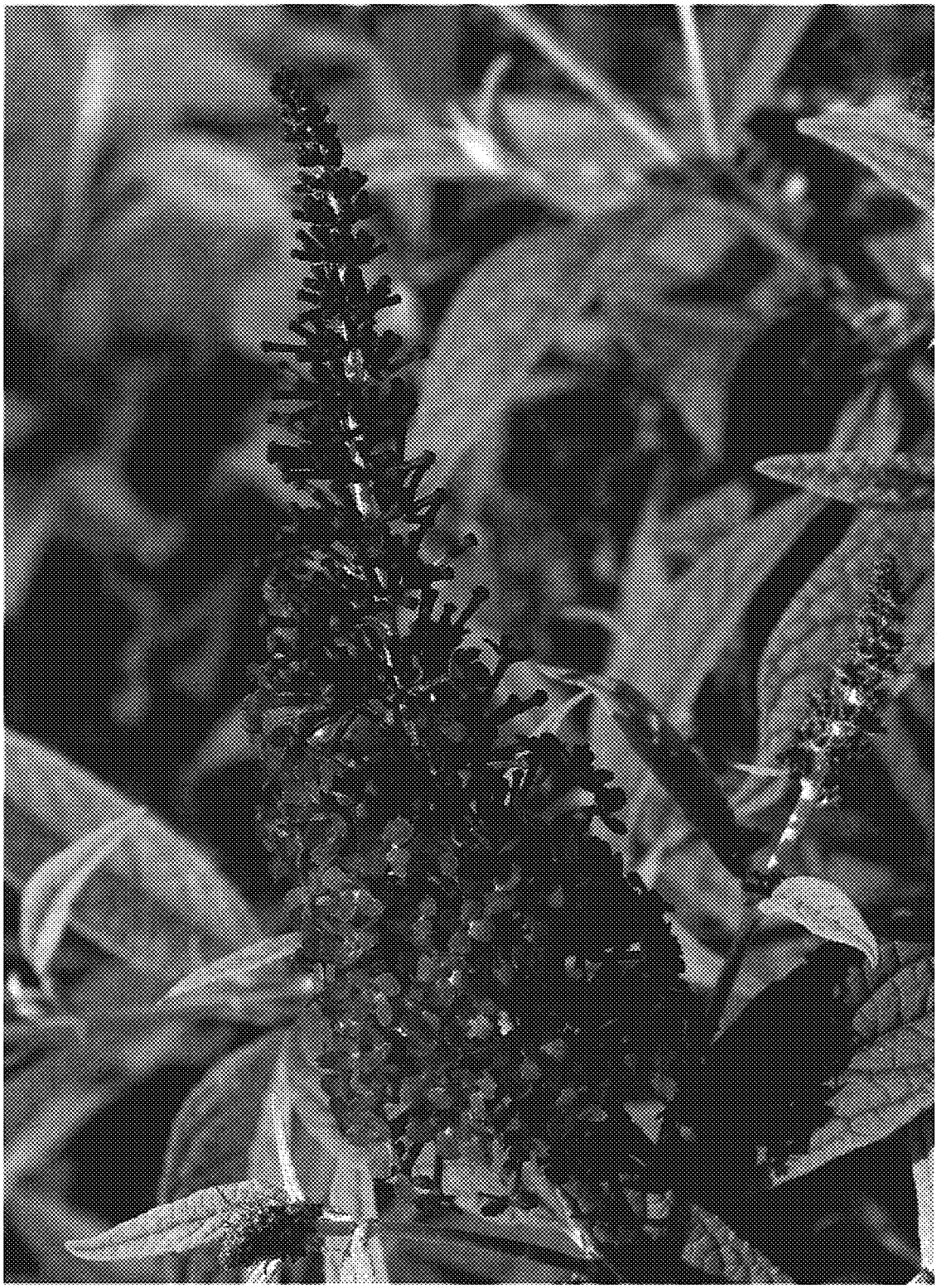

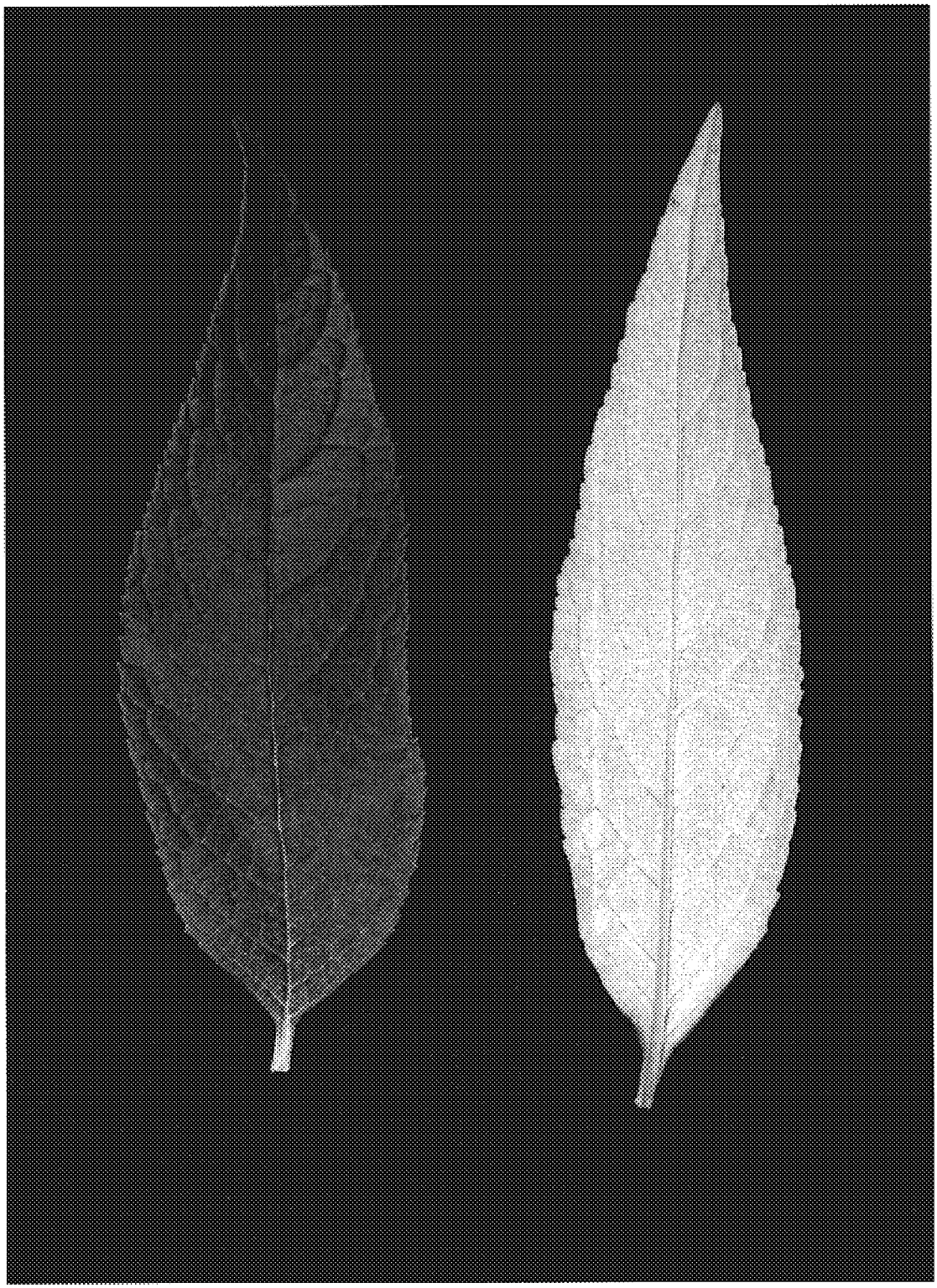

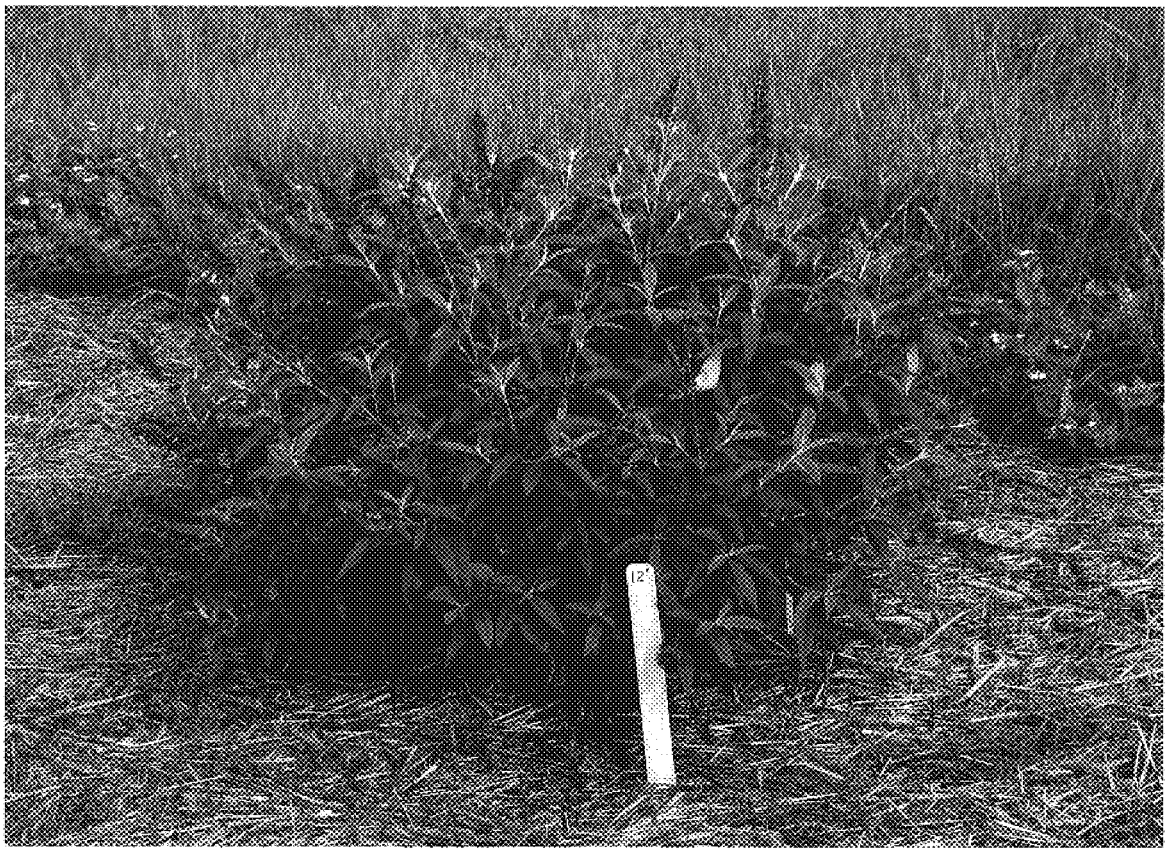
12'